United States Patent [19]

Irwin et al.

[11] Patent Number: 4,942,873

[45] Date of Patent: Jul. 24, 1990

[54] RESUSCITATION DEVICE

[76] Inventors: Lawrence F. Irwin, 12860 San Fernando Rd., Sylmar, Calif. 91342; Frank R. Irwin, P.O. Box 636, Oceano, Calif. 93445

[21] Appl. No.: 245,561

[22] Filed: Sep. 16, 1988

Related U.S. Application Data

[63] Continuation-in-part of Ser. No. 938,419, Dec. 5, 1986, abandoned.

[51] Int. Cl.⁵ ............................................. A61M 16/00
[52] U.S. Cl. .......................... 128/203.11; 128/205.24; 128/912
[58] Field of Search ..................... 128/202.28, 202.29, 128/203.11, 205.24, 912; 132/844; 288/921

[56] References Cited

U.S. PATENT DOCUMENTS

| 15,192 | 6/1856 | Peale | 132/844 |
| 2,882,104 | 5/1959 | Sovinsky et al. | 128/203.11 |
| 3,957,046 | 3/1976 | Harris | 128/203.11 |
| 4,619,640 | 10/1986 | Porolsky et al. | 128/203.11 |

FOREIGN PATENT DOCUMENTS

| 798660 | 11/1968 | Canada | 128/205.24 |
| 1201930 | 1/1960 | France | 128/203.11 |

Primary Examiner—Randall L. Green
Assistant Examiner—K. M. Reichle
Attorney, Agent, or Firm—James E. Brunton

[57] ABSTRACT

A mouth-to-mouth resuscitation device embodying a novel, one piece resiliently deformable valving member which permits flow of air through the device in a direction toward the patient but effectively blocks flow of air and fluids in the opposite direction.

7 Claims, 3 Drawing Sheets

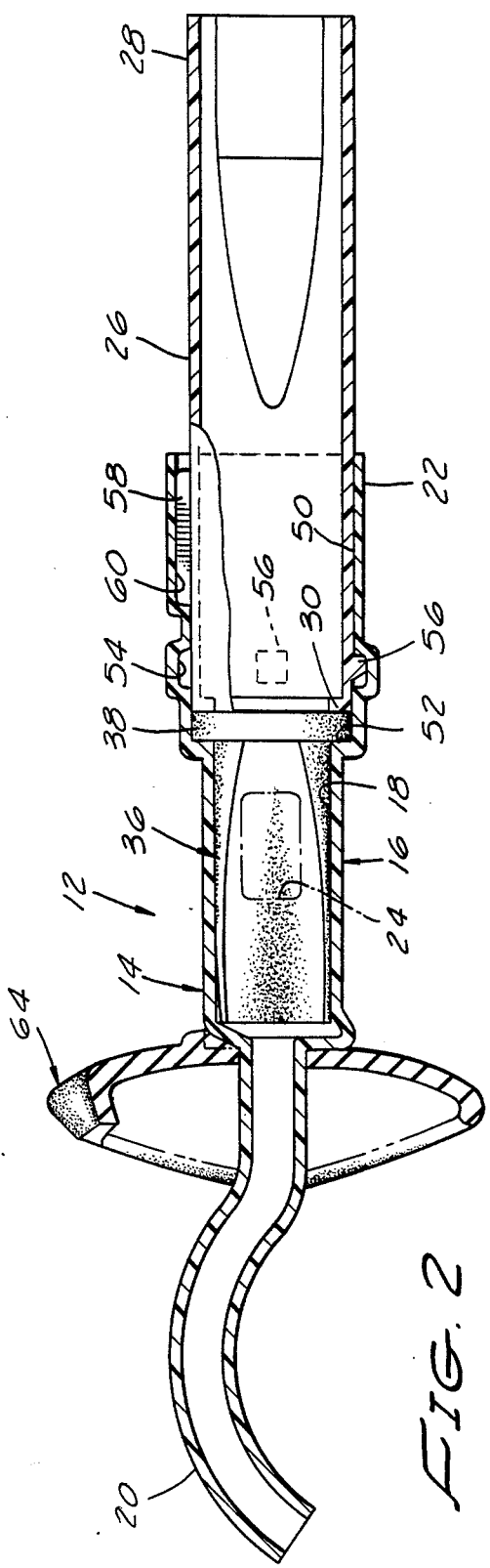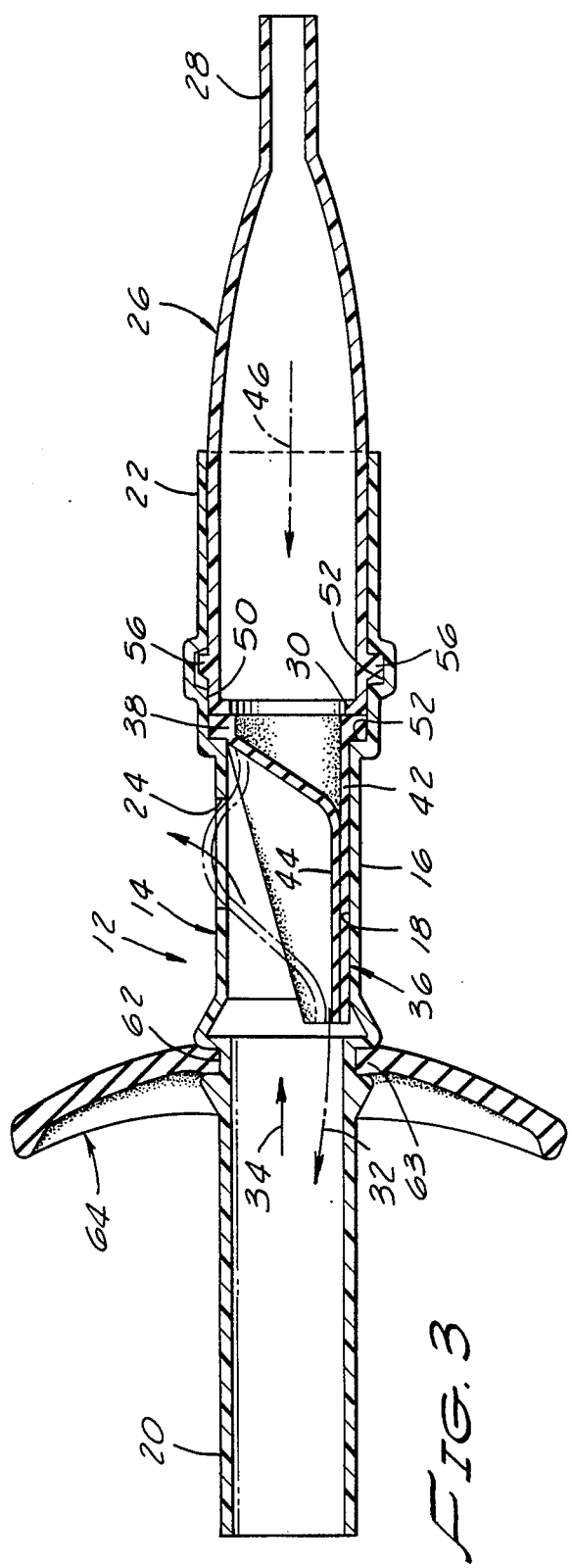

RESUSCITATION DEVICE

BACKGROUND OF THE INVENTION

This is a Continuation In Part Application of Application Ser. No. 06,938,419, filed Dec. 5, 1986 now abandoned.

FIELD OF THE INVENTION

The present invention relates generally to mouth-to-mouth resuscitation devices. More particularly, the invention concerns a resuscitation device embodying a novel valving member which permits flow of air through the device in a direction toward the patient but effectively blocks flow of air and fluids in the opposite direction.

DISCUSSION OF THE PRIOR ART

Mouth-to-mouth resuscitation is a valuable, life saving expedient when properly accomplished. However, in the past, the procedure has not been wholly satisfactory for several reasons including the natural repugnance most people have of placing their mouth in contact with the patient's mouth knowing that the patient is likely to vomit during the procedure. In recent times, the possibility of transmission by the patient of acquired immune deficiency, oral herpes and other serious diseases has caused people to avoid giving mouth-to-mouth resuscitation. Finally, the difficulty of practicing the procedure properly causes people to shy away from even attempting to render assistance.

Because of problems of the character outlined in the preceding paragraph, many types of devices have been suggested to allegedly simplify the administration of mouth-to-mouth resuscitation and to avoid the spread of germs. However, most of these prior art devices are cheap, ineffective gadgets.

Some of the more effective prior art devices of which the present inventor is aware includes those disclosed in U.S. Pat. Nos. 3,957,046 issued to Harris; 4,106,502 issued to Wilson and 4,535,765 issued to Pavluceio et al. The device of the present invention is readily distinguishable from these prior art disclosures because of the unique valving arrangement embodied within the device. This novel device permits air to flow toward the patient but precludes the flow of air and fluids back to the person administering the mouth-to-mouth resuscitation.

SUMMARY OF THE INVENTION

It is an object of the present invention to provide a mouth-to-mouth resuscitation device having a pair of tubular members jointed together end-to-end with a valving mechanism therebetween to permit the flow of breathed air to the victim or person being resuscitated but not permitting any exhaled air or vomit from the victim coming into contact with the other person.

Another object of the present invention is to provide a device of the aforementioned character in which the valving mechanism is of simple construction but yet is highly reliable in use.

Another object of the invention is to provide a valve device in which the valving means will automatically seal the exhaled air outlet formed in one of the tubular members during inflow of air to the victim, thus eliminating the need to manually block the air outlet with a finger on a hit-or-miss frequency.

A further object of the present invention is to provide a mouth-to-mouth resuscitation device that is simple in construction and design, consisting of a minimum of parts and of such low cost that the device is disposable thereby eliminating the need to sterilize it to permit reuse thereof.

In summary, as will be better understood from the description which follows, the mouth-to-mouth resuscitating device of the present invention comprises a first tubular member having a wall defining an inner, longitudinally extending surface and first and second end portions, the wall having an aperture therethrough to expel vomit or fluids from the patient; a second tubular member having first and second end portions, the second member being operably interconnected and substantially coaxially aligned with said first member and valving means carried within the first tubular member and disposed intermediate said first and second end portions thereof for permitting the flow of air through said first tubular member in first direction, but blocking the flow of fluids therethrough in the opposite second direction. The valving means comprises an annular portion and a yieldably deformable wall connected to and extending outwardly from the annular portion, the wall having a first portion normally disposed in close engagement with the longitudinally extending surface of said first tubular member and a second portion normally disposed in a first position in close engagement with the first portion of the yieldably deformable wall the second portion being yieldably deformable in response to fluid pressure to a second position to permit the flow of fluids toward the patient.

BRIEF DESCRIPTION OF THE DRAWINGS

FIG. 2 is a side elevational cross-sectional view of the resuscitator of the present invention.

FIG. 3 is a top cross-sectional view of the resuscitator illustrating in phantom lines the operation of the valving mechanism of the device.

DESCRIPTION OF THE INVENTION

Figure 1:
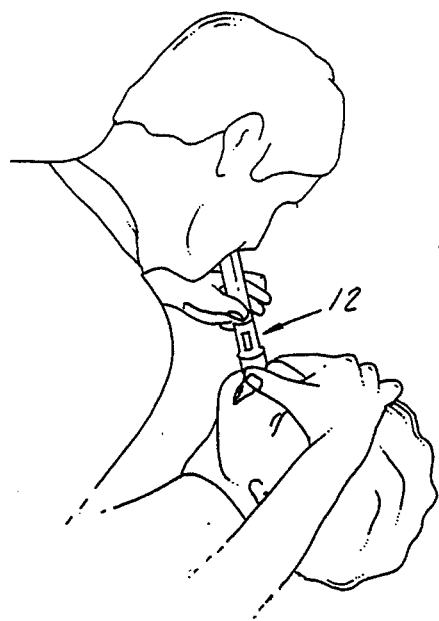
FIG. 1 is generally schematic view illustrating the use of the mouth-to-mouth resuscitating device of the present invention.

Referring to the drawings and particularly to FIGS. 1, 2 and 3, the mouth-to-mouth resuscitating device of the present invention is generally designated by the numeral 12. The device comprises a first tubular member 14 having a cylindrically shaped section 16 defining an inner longitudinally extending surface 18. First tubular member 14 has a first end portion 20 and a second end portion 22. As best seen in FIGS. 2 and 3, tubular portion 16 of the first member is provided with an aperture 24 extending through the wall of the tubular section defining radially extending edge portions as best seen in FIG. 3.

Operably associated with first member 14 is a second tubular member 26. Member 26 has a first end portion 28 and a second end portion 30. As indicated in FIGS. 1 and 2, second end portion 30 of tubular member 26 is telescopically receivable within second end portion 22 of first member 14. When the first and second members are mated in the manner shown in FIGS. 2 and 3, they are coaxially aligned and releasably interconnected by interconnection means, the details of which will presently be described.

Forming a highly important aspect of the present invention is valving means carried within first tubular member 14 and disposed intermediate the first and second end portions thereof for permitting the flow of air through the tubular member 14 in a first direction as indicated by the arrow 32 in FIG. 3, but blocking the flow of fluids through the valve in the opposite, second, direction indicated by the arrow 34.

Figure 4:
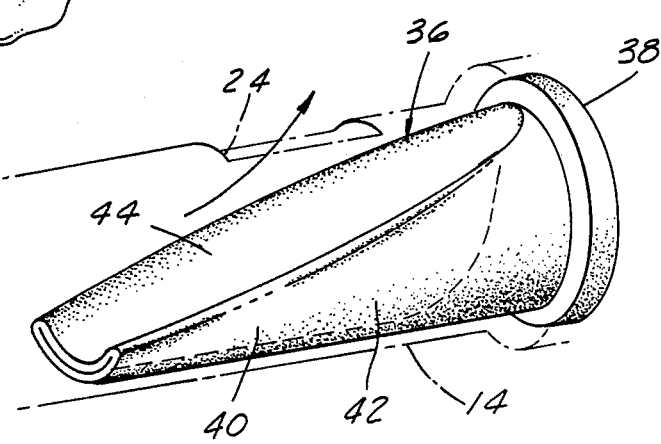
FIG. 4 is an enlarged perspective view illustrating the configuration of the valving mechanism in its normal closed position.
Figure 5:
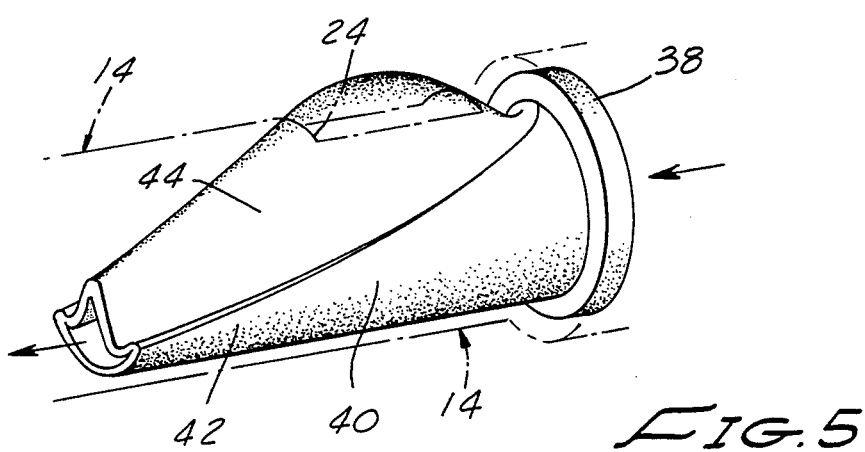
FIG. 5 is a perspective view similar to FIG. 4 but showing the valve in its open position permitting the flow of air therethrough toward the patient.
Figure 6:
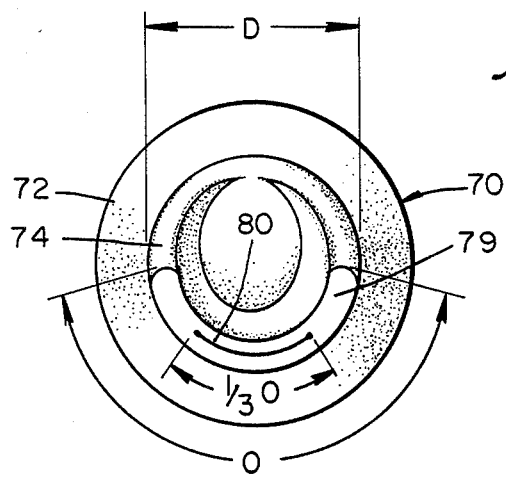
Figure 7:
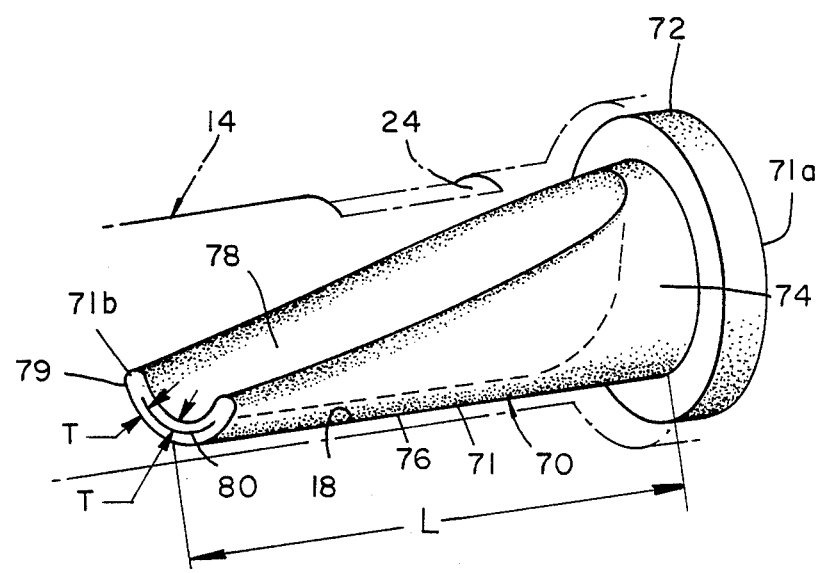
Figure 8:
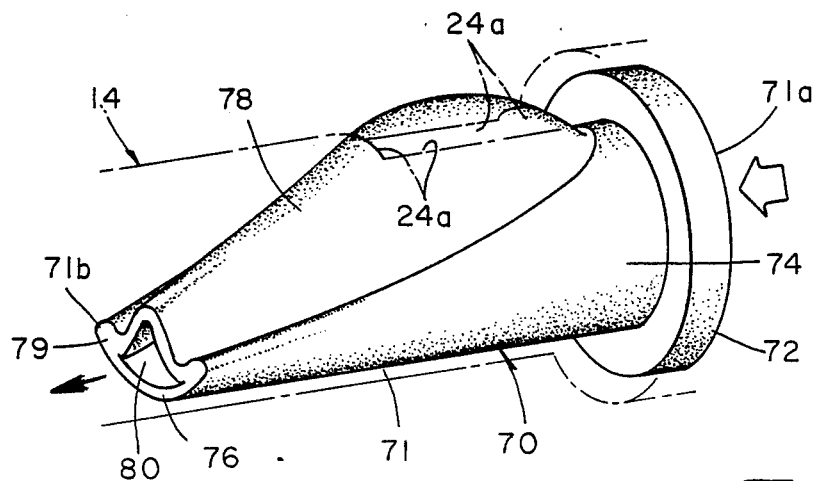

Referring to FIGS. 4 and 5, in the present embodiment of the invention the valving means is provided as an integrally formed member 36 constructed of a resilient material such as rubber, neoprene, silicone or the like. Valve member 36 comprises an annular shaped, substantially rigid portion 38 and a deformable wall 40 connected to, and extending outwardly from, annular portion 38. Wall 40 has a first portion 42 which is normally disposed in close engagement with the longitudinally extending surface 18 of the first tubular member 14 (FIG. 3) and a second portion 44 normally disposed in a first position in close engagement with first portion 42 of the yieldably deformable wall 40.

As illustrated in FIGS. 4 and 5, second portion 44 of wall 40 is yieldably deformable in response to air pressure from the first closed position shown in FIG. 4 to the inflated, or outwardly extending, position shown in FIG. 5. Referring to FIG. 3, the solid lines illustrate the valve configuration in its normal closed position with the second portion 44 of the wall in close engagement with the first portion 42 of the wall. However, upon the flow of air through the device in the direction of the arrow designated by the numeral 46, the valve will move to its open position with second wall portion 44 moving into the orientation shown by the phantom lines in FIG. 3. It is important to note that in this expanded or ballooned position, second wall 44 moves into closing engagement with the edges of aperture 24 thereby sealing the aperture and preventing any flow of fluids therethrough in the direction of the arrow generally designated by the numeral 48. The purpose of this important aperture sealing feature will be discussed in the section which follows entitled "Operation".

As best seen by referring to FIG. 3, first tubular member 14 is provided with an enlarged diameter portion 50 which is adapted to closely receive annular shaped portion 38 of the valving member. With portion 38 of the valving member in position within enlarged diameter portion 50 and in engagement with a shoulder 52 at the juncture of the enlarged diameter portion and portion 16 of the first valving member, second end portion 30 of second member 26 can be moved into clamping engagement with the valving member thereby sealably securing the valving means within the assemblage formed by the first and second valve members.

Also provided with first tubular member 14 is a circumferential, internal groove 54. Closely receivable within groove 54 are circumferentially spaced protuberances 56, which protuberances form a part of the interconnection means of the embodiment of the invention shown in the drawings. Protuberances 56 are of a size such that they will pass through the first end portion 22 of the first member as the walls are yieldably outwardly deformed. In this way second member 26 can be telescopically received within the first end of the first member and mateably inserted until the protuberances snap into the circumferential groove 54. Once disposed within the groove, the protuberances will function to prevent accidental separation of the parts. As indicated in FIG. 3, the side walls of the circumferential groove 54 are slightly tapered so that a separating force exerted on the first and second tubular members will cause a deformation of the first end portion 22 of the first member sufficient to permit the protuberances 56 to be moved free of the circumferential groove thereby enabling separation of the first and second tubular members.

Forming another part of the interconnection means of the present invention is an alignment means for aligning the first and second tubular members in a predetermined rotational orientation. In the embodiment of the invention shown in the drawings, this alignment means comprises a longitudinally extending protuberance 58 formed on second member 26 intermediate its ends. Longitudinally extending protuberance 58 is closely receivable within longitudinally extending internal channel 60 formed in first member 14 proximate circumferential groove 54. Upon mating the first and second tubular members so that protuberances 56 will snap into circumferentially extending groove 54, a relative rotational movement between the first and second tubular members will cause protuberance 58 to snap into longitudinally extending channel, or cavity, 60 thereby locking the components against further accidental rotation with the parts thus rotationally aligned the end portions 20 and 28 of the first and second members will be correctly operationally aligned.

As best seen in FIG. 3, first member 14 is provided with an external circumferentially extending groove 62 which closely receives a central flange 63 formed on a breathing mask 64. Breathing mask 64 functions to close off the entire mouth of the victim to compel the air being breathed into the mouth to flow into the lungs and not escape at the sides of the mouth which must be open to receive portion 20. Breathing mask 64 is preferably made of a yieldably soft plastic or rubber material which will snap into circumferentially extending groove 62 and will tend to closely conform to the patient's face during use.

Operation

Using the device of the present invention for emergency resuscitation, the victim's mouth is opened and the curved end 20 of tubular member 14 is placed on his tongue and then slid inwardly until the breathing mask 64 engages the victim's face. The person performing the resuscitation then places the thumb and finger of one hand about the victim's nose to close off the nostrils and blows into the mouthpiece 28. The air pressure flowing in the direction of the arrow 46 of FIG. 3 will cause the valving means to move into the open position shown by the phantom lines in FIG. 3 to permit air to flow into the first tubular member and then into the patient through curved end 20. As indicated in FIG. 3, deformation of the valving member also sealably closes the aperture 24 thereby preventing leakage of air through the aperture. This ensures that all of the air being breathed into the device by the person performing the resuscitation reaches the lungs of the patient. Between breaths the nostrils are released to permit the victim to exhale. When the victim exhales, or when the person performing the resuscitation ceases to force air into the device, the valving means will automatically move into its closing position shown by the solid lines in FIG. 3. In this position, the valve will prevent any flow of fluid or air in the reverse direction, that is in a direction toward the person performing the resuscitation. Air from the victim, or any fluids emitted from the patient, such as vomit, will pass through the aperture 24 and never reach the person providing the emergency assistance.

As earlier pointed out, the materials and manufacturing costs of the device of the invention are very low thereby permitting the device to be discarded after each use. However, if it is desired to reuse the device, the device can easily be disassembled and the component parts thereof sterilized as by boiling. Similarly, due to the ease of disassembly of the device, it is a simple matter to replace the valving mechanism at any time with a new valving mechanism.

An extremely important feature of the specially designed valving mechanism of the invention resides in the novel configuration of the cooperating wall portions 42 and 44 and the arrangement of the fluid outlet port of the valve. In using the device of the invention it is absolutely essential that the aperture 24 in the side wall of member 14 be positively sealed during controlled delivery of air to the patient to prevent undesirable inflow of air from atmosphere. This important feature of the valving mechanism is best illustrated in FIG. 5 of the drawings.

One of the major drawbacks of prior art devices which embody the so-called duck valve type valving mechanism is the fact that during the air delivery cycle the duck valve, because of its basic construction and lack of controlled impedance to fluid flow toward the patient, cannot be relied upon to automatically and positively close the exhale and expectorating discharge port typically provided in the wall of the proximal portion of the device. In point of fact, a geometrical analysis of a prior art duck valve of the character in which the closed end extends across the entire diameter of the tube in which the valve is carried, at once reveals that the valve can only expand to approximately two-thirds of the circumference of the tube. Accordingly, a discharge port in the wall of the tube cannot be reliably closed by the duck valve construction. Unless the fluid discharge port of the device is positively sealed during delivery of air to the patient as is permitted only by the unique construction of the valve of the present invention, precisely regulated and controlled delivery of air to the patient cannot be achieved during resuscitation.

Referring particularly to FIGS. 3 and 5, the valving means of the present invention uniquely overcomes the drawbacks of prior art duck valve mechanisms used in resuscitator devices by carefully controlling the configuration of the valve and the size of the fluid or air outlet relative to the interior volume of the valve mechanism. Without proper design, the valving mechanism will not balloon out in the manner shown in FIG. 5 so as to properly seal the edges of aperture 24.

As illustrated in FIG. 5, second portion 44 of wall 40 is yieldably deformable in response to controlled air pressure flowing in the direction of the arrow through the valve outlet so that portion 44 moves from the first closed position shown in FIG. 4 to the inflated, or outwardly extending, position shown in FIG. 5.

Experience has shown that in order to positively ensure that second wall portion 44 will repeatedly balloon into positive sealing engagement with the edges of aperture 24, the geometry of the valve, including the shape of cooperating wall portions 42 and 44 and the size of the valve outlet must be carefully controlled. If the geometry is improper, the valve will act somewhat like a duck valve and the wall will tend to flutter and accordingly imperfectly seal aperture 24. If the valve outlet is too small insufficient delivery of air to the patient will result. By carefully controlling the size of the valve outlet and the configuration of the nesting wall portions, precisely proper "ballooning" of wall 44 as shown in FIG. 5 will result so that an optimum in flow of air to the patient will occur and at the same time a positive sealing of aperture 24 will be achieved.

In summary, in the manufacture of the valving member of the invention, great care must be taken to control the valve geometry so as to insure proper impedance to the flow of air through the device to cause the vital ballooning function. In controlled operation of the device of the invention embodying this unique geometry, air flowing toward the patient through a valve outlet having an arcuate length appreciably less than the length of arcuate end wall will cause the wall portion 44 to correctly protrude through aperture 24 in the manner shown in FIG. 5 and to positively seal against edges of aperture 24 thereby positively closing the aperture. In this way undesirable flow of air through aperture 24 due to back pressure will be positively and reliably prevented during the precisely controlled delivery of air to the patient. When the air delivery cycle ends, the valve will quickly return to the closed configuration shown in FIG. 4.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A mouth-to-mouth resuscitating device comprising:
   (a) an elongated, first tubular member having a first, open, end portion for engagement with a victim's mouth, a second open, end portion and an elongated, annular-shaped wall extending therebetween having a cylindricallyshaped section, defining longitudinally-extending, first and second, oppositely-disposed inner, concave surfaces, said wall having an aperture through said second, inner, concave surface defining edge portions;
   (b) a second tubular member having a first, open, end portion for engagement with a rescuer's mouth and a second, open, end portion;
   (c) interconnection means for releasably interconnecting said first and second tubular members in coaxial alignment proximate the second end portions thereof; and
   (d) valving means mounted within said first tubular member and disposed intermediate said first and second end portions thereof for permitting the flow of fluids through said first tubular member in a first direction, but blocking the flow of fluids through the valving means in the opposite, second, direction while urging fluid flow through the aperture in said wall of said first tubular member, said valving means comprising an integrally formed member including:
   (i) a ring-shaped portion;

(ii) a yieldably, deformable wall, including an annular portion having opposite ends and coaxially connected at one end to said ring-shaped portion and extending outwardly from said ring-shaped portion toward said first portion of said first tubular member at the other end, a first, longitudinally extending portion having a concave, inner surface and a convex, outer surface normally disposed in parallel, nesting engagement with said longitudinally-extending, first, concave inner surface of said annular-shaped wall of said first tubular member and a second, longitudinally-extending portion having a convex, outer surface and a concave, inner surface substantially coextensive with and normally, its first position, disposed in parallel, nesting engagement with said concave, inner surface of said first portion of said yieldably deformable wall, said second portion of said wall yieldably deforming towards said second, concave, inner surface of said annular-shaped wall of said first tubular member and sealably engaging with the edges of said aperture in response to fluid flow in the first direction, its second position, thereby positively blocking the flow of air through said aperture yet permitting the flow of fluids through said first tubular member in said first direction; and (iii) means for sealably connecting said annular portion of said yieldably deformable wall with said ring-shaped portion to provide a fluid-tight seal therebetween.

2. A device as defined in claim 1 in which said ring-shaped portion of said valving means is sealably clamped between said second end portions of said first and second tubular members in coaxial alignment therewith when said first and second members are releasably interconnected by said interconnection means.

3. A device as defined in claim 1 in which said first end portion of each of said first and second tubular members is tapered for insertion into the mouths of persons using the device.

4. A device as defined in claim 3 in which said first end portion of said first tubular member is curved along its length.

5. A mouth-to-mouth resuscitation device comprising:

(a) a first tubular member having first and second open, end portions and an elongated wall extending therebetween defining first and second, oppositely disposed, longitudinally-extending surfaces which are concave in cross-section, said second surface having an aperture therethrough open to ambient, said first end portion of said first tubular member being engageable with a victim's mouth;

(b) a second tubular member having first and second, open, end portions, said first end portion of said second tubular member being engageable with a rescuer's mouth;

(c) interconnection means for releasably interconnecting said first and second tubular members in coaxial alignment proximate the second ends portion thereof; and (d) valving means mounted within said first tubular member and disposed intermediate said first and second end portion thereof for permitting the flow of fluids through said first tubular member in a first direction, but blocking the flow of fluids through the valving means in the opposite, second, direction, said valving means comprising a generally tubular-shaped body having first and second, longitudinally-spaced, ends, said member being constructed of a resilient material and including;

(i) a ring-shaped portion at the first end;

(ii) a yieldably, deformable, longitudinally-extending, wall portion, including an annular portion having opposite ends and coaxially connected at one end to the ring-shaped portion and extending outwardly from said first end portion of said first tubular member at the other end, a first, longitudinally-extending portion having a concave, inner surface and a convex, outer surface normally disposed in parallel, nesting engagement with said longitudinally-extending inner surface, of said first tubular member and a second, longitudinally-extending portion having a convex, outer surface and a concave, inner surface substantially coextensive with and normally, its first position, disposed in parallel, nesting engagement with the concave, inner surface of said first portion, said first and second portions of said wall normally engaging at said second end of said body so as to define an arcuately-shaped end in cross section, said second portion yieldably deforming away from said first portion to a second, ballooned-out, position to sealably engage with the aperture and define with said first portion an air outlet means of a predetermined size at said second end in response to fluid flowing in the first direction, thereby positively blocking the flow of air through said aperture yet permitting the flow of fluids through said first member in said first direction; and (iii) means for sealably connecting said annular portion of said yieldably, deformable, wall portion with said ring-shaped portion to provide a fluid-tight seal therebetween.

6. A mouth-to-mouth resuscitation device as defined in claim 5 in which, said air outlet means resists air flow therethrough and causes said second portion of said body to extend radially outwardly through said aperture in the second position.

7. A mouth-to-mouth resuscitation device as defined in claim 6 in which said air outlet means comprises a generally arcuate slit having a length substantially less than the length of said arcuately-shaped end.

* * * * *